US012708796B2

(12) United States Patent
Meijers et al.

(10) Patent No.: US 12,708,796 B2
(45) Date of Patent: Aug. 18, 2026

(54) RADIATION TREATMENT PLANNING THAT CONSIDERS THE DIMENSIONS OF VOLUMES IN A TREATMENT TARGET

(71) Applicant: Varian Medical Systems Particle Therapy GmbH & Co. KG, Troisdorf (DE)

(72) Inventors: Artures Meijers, Overath (DE); Christel Smith, Santa Barbara, CA (US); Michiko Rossi, Espoo (FI)

(73) Assignees: SIEMENS HEALTHINEERS INTERNATIONAL AG, Cham (CH); VARIAN MEDICAL SYSTEMS, INC., Palo Alto, CA (US); VARIAN MEDICAL SYSTEMS PARTICLE THERAPY GMBH & CO. KG, Troisdorf (DE)

( * ) Notice: Subject to any disclaimer, the term of this patent is extended or adjusted under 35 U.S.C. 154(b) by 1269 days.

(21) Appl. No.: 17/562,843

(22) Filed: Dec. 27, 2021

(65) Prior Publication Data

US 2023/0201628 A1 Jun. 29, 2023

(51) Int. Cl.
*A61N 5/10* (2006.01)

(52) U.S. Cl.
CPC .................................. *A61N 5/1031* (2013.01)

(58) Field of Classification Search
CPC .......... A61N 5/1031; A61N 2005/1087; A61N 5/1043; A61N 5/103
See application file for complete search history.

(56) References Cited

U.S. PATENT DOCUMENTS

| | | | | |
|---|---|---|---|---|
| 11,020,616 | B2 | 6/2021 | Engwall et al. | |
| 2015/0090894 | A1* | 4/2015 | Zwart | H05H 13/02 250/396 ML |
| 2017/0216622 | A1* | 8/2017 | Fujitaka | A61N 5/103 |
| 2019/0022409 | A1* | 1/2019 | Vanderstraten | A61N 5/1081 |
| 2020/0129782 | A1 | 4/2020 | Stal et al. | |

FOREIGN PATENT DOCUMENTS

| | | | |
|---|---|---|---|
| EP | 3646921 A1 | 5/2020 | |
| WO | WO-2019016301 A1 * | 1/2019 | A61N 5/1031 |

* cited by examiner

*Primary Examiner* — Carrie R Dorna
*Assistant Examiner* — Joshua Darryl D Lannu
(74) *Attorney, Agent, or Firm* — Harness, Dickey & Pierce, P.L.C.

(57) ABSTRACT

For planning radiation treatment using spot scanning, also known as pencil beam scanning, the size and/or shape of the treatment target is considered when determining the placement and density of spots in the treatment target. For example, when generating a radiation treatment plan, the size and/or shape of the treatment target can be considered when determining the placement and density of spots in the treatment target. During treatment planning, the treatment target can be separated into regions corresponding to different target volumes in the treatment target, and the placement and density of spots (the amount of spacing between spots) in each region can be determined independently for each region according to the size and/or shape of the region.

21 Claims, 7 Drawing Sheets

RADIATION TREATMENT PLANNING THAT CONSIDERS THE DIMENSIONS OF VOLUMES IN A TREATMENT TARGET

BACKGROUND

The use of radiation therapy to treat cancer is well known. Typically, radiation therapy involves directing a beam of high energy proton, photon, ion, or electron radiation into a target volume in a treatment target of unhealthy tissue (e.g., a tumor or lesion).

Radiation therapy using proton beams has a significant advantage relative to the use of other types of beams. A proton beam reaches a depth in tissue that depends on the energy of the beam, and releases most of its energy (delivers most of its dose) at that depth. The region of a depth-dose curve where most of the energy is released is referred to as the Bragg peak of the beam.

Before a patient is treated with radiation, a treatment plan specific to that patient is developed. The plan defines various aspects of the radiation therapy using simulations and optimizations that may be based on past experiences. In general, the purpose of the treatment plan is to deliver sufficient radiation to unhealthy tissue while minimizing exposure of surrounding healthy tissue to that radiation.

One radiation therapy technique is known as spot scanning, also known as pencil beam scanning. In spot scanning, a beam is directed to spots in a treatment target as prescribed by the treatment plan. The prescribed spot locations are typically arranged in a fixed (raster) pattern for each energy layer of the beam, and the beam is delivered on a fixed scanning path within an energy layer. By superposition of several beams of different energies at neighboring spots, the Bragg peaks of the beams overlap to deliver the prescribed dose across the treatment target up to the edges of the target, with a sharp drop to zero dose beyond the edges.

A precise calculation of the number of spots and their placement (location and distribution) is critical. The goal is to determine a spot placement that: conforms to the outline of the treatment target, to improve the lateral penumbra and spare healthy tissue outside the treatment target from exposure to radiation beyond what is necessary to treat the unhealthy tissue; and is uniform inside the treatment target, to avoid dose variations (dose inhomogeneity) inside the treatment target so that the prescribed dose is delivered to all parts of the target.

When generating a treatment plan, an initial spot pattern or grid is specified for the entire treatment target, and the plan is optimized by adjusting the weights of the spots in the pattern. The number of spots in the initial spot pattern is kept as low as possible to reduce the time it takes to optimize the plan and to achieve a high quality plan with respect to dosimetry. If there are too many spots in the initial spot pattern, then the optimizer tool may not be able to converge on a solution in which the spots are properly weighted to deliver a homogeneous dose across the treatment target. Also, if the initial spot pattern includes a large number of spots, then the final treatment plan may also include many spots, thus lengthening the treatment time (dose delivery time) to the detriment of the patient.

For multiple clinical indications, treatment plans may have to be optimized to cover different target volumes in the treatment target that may be separated from one another and that may differ significantly in size. For example, with reference to FIG. 1, the treatment target in a breast cancer patient may include a relatively large first target volume 101 corresponding to the breast, and a much smaller second target volume 102 or node (an involved node). In addition, the second target volume 102 may be separated from the first target volume 101; that is, there may be healthy tissue between the two target volumes. As mentioned above, the goal is to keep the number of spots in the initial spot pattern as low as possible. That can result in situations in which a relatively small target volume (e.g., the second target volume 102) is not sufficiently covered by the initial spot pattern or in which the pattern may extend beyond the edge of the volume, as illustrated in the example of FIG. 1. Consequently, during treatment, the smaller target volume may receive an insufficient or non-uniform dose. Also, the conformity of the dose to the treatment target in general and the smaller target volume in particular may be suboptimal; that is, healthy tissue outside the targeted areas, including organs-at-risk (e.g., the heart), may be exposed to radiation.

SUMMARY

Embodiments according to the present invention apply methodologies not conventionally used for spot placement to develop radiation treatment plans for spot scanning (e.g., pencil beam scanning). More specifically, when generating a radiation treatment plan, the size and/or shape of the treatment target is considered when determining the placement and density of spots in the treatment target. In embodiments, during treatment planning, the treatment target is separated into regions corresponding to different target volumes in the treatment target, and the placement and density of spots (the amount of spacing between spots) in each region are determined independently for each region according to the size and/or shape of the region. By properly weighting the spots with respect to, for example, beam energy or dose, a uniform dose is applied across each treatment volume and hence across the entire treatment target.

For example, if the treatment target includes a larger target volume and a smaller target volume (where the two volumes may or may not be physically separated from each other), then the amount of distance between spots in the region corresponding to the larger target volume can be greater than the amount of distance between spots in the region corresponding to the smaller target volume. That is, the smaller region/target volume has a higher density of spots relative to the larger region/target volume. Similarly, if the treatment target includes a relatively narrow target volume extending from a larger (e.g., wider) target volume, then the amount of distance between spots in the region corresponding to the larger target volume can be greater than the amount of distance between spots in the region corresponding to the narrower target volume. That is, the narrower region/target volume has a higher density of spots relative to the larger region/target volume.

Accordingly, the treatment planning system has sufficient freedom to independently optimize the weights of the spots in each target volume of the treatment target. Consequently, during treatment, each target volume will receive a homogenous dose, and the delivered dose will conform more closely to the edges of the target volumes and hence to the edges of the entire treatment target. This can be particularly important for cases such as, but not limited to, breast cancer patients due to the proximity of smaller target volumes (e.g., parasternal nodes) to organs-at-risk (e.g., the heart) as in the example of FIG. 1. This can also be particularly important in cases where the treatment target has a complex shape such as, but not limited to, head and neck cancer patients (elective target volumes) and Hodgkin lymphoma patients.

Furthermore, the robustness of treatment plans is maintained or improved. That is, radiation treatments are generally administered over a period of time (e.g., weeks), and treatment plans generated as disclosed herein are more tolerant to changes in patient position or anatomy during the treatment period.

Embodiments according to the present invention provide improved methods that can be used for generating radiation treatment plans for radiation therapy (RT) including FLASH RT. For FLASH RT, dose rates of at least 40 grays (Gy) in less than one second, and as much as 120 Gy per second or more, may be used.

These and other objects and advantages of embodiments according to the present invention will be recognized by one skilled in the art after having read the following detailed description, which are illustrated in the various drawing figures.

This summary is provided to introduce a selection of concepts that are further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments according to the present disclosure and, together with the detailed description, serve to explain the principles of the disclosure. The drawings are not necessarily drawn to scale.

DETAILED DESCRIPTION

Figure 1:
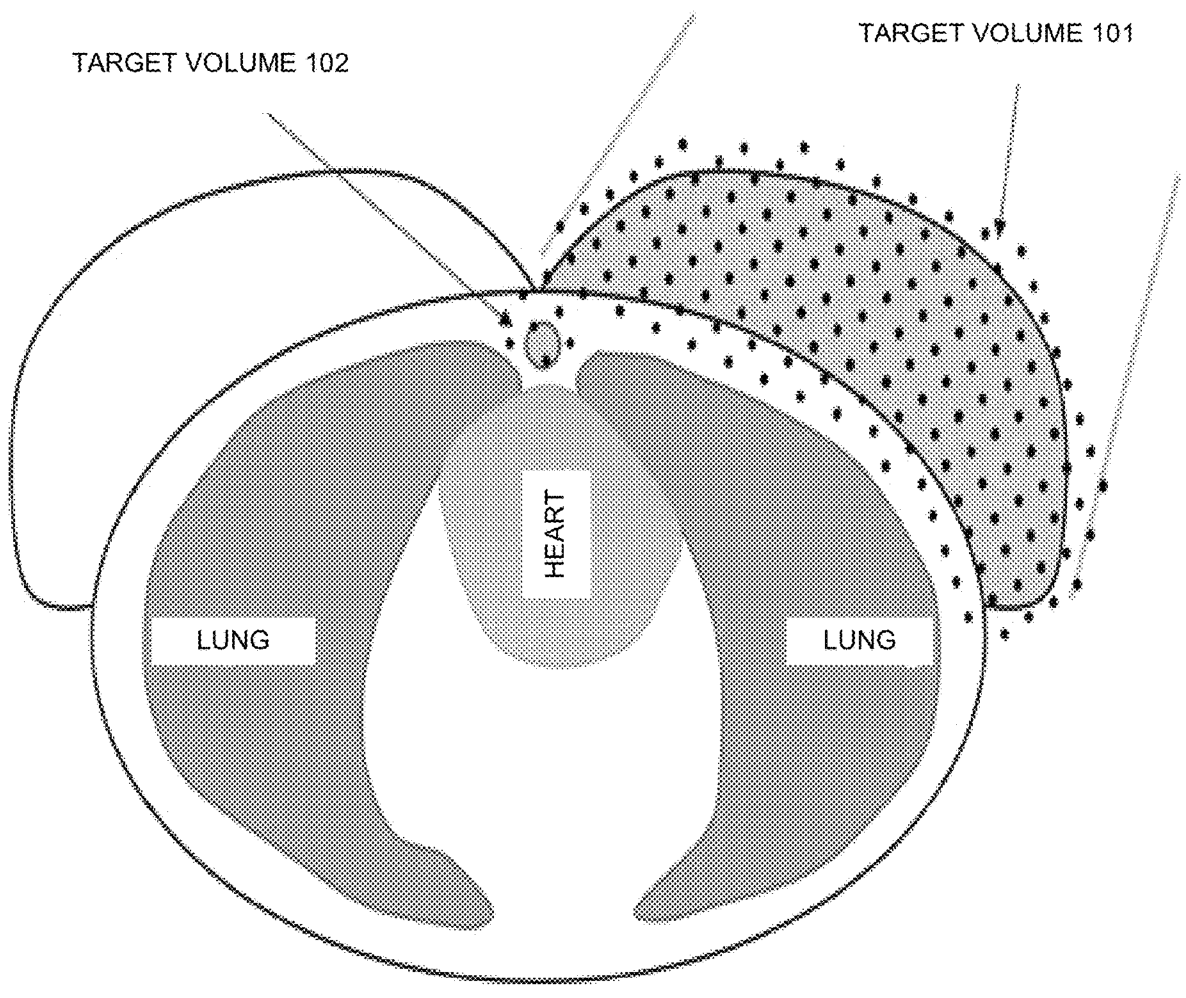
FIG. 1 illustrates an example of a cross-section of a treatment target that is modeled using a conventional method.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "accessing," "determining," "storing," "assigning," "adjusting," or the like, refer to actions and processes (e.g., the flowchart 700 of FIG. 7) of a computer system or similar electronic computing device or processor (e.g., the computer system 200 of FIG. 2). The computer system or similar electronic computing device manipulates and transforms data represented as physical (electronic) quantities within the computer system memories, registers or other such information storage, transmission or display devices.

The discussion to follow may include terms such as "dose," "dose rate," etc. Unless otherwise noted, a value is associated with each such term. For example, a dose has a value and can have different values. For simplicity, the term "dose" may refer to a value of a dose, for example, unless otherwise noted or apparent from the discussion.

Portions of the detailed description that follows are presented and discussed in terms of methods or processes. Although operations and sequencing thereof are disclosed herein, such operations and sequencing are examples only. Embodiments are well-suited to performing various other operations or variations of the operations described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory, read only memory (ROM), electrically erasable programmable ROM (EEPROM), flash memory or other memory technology, compact disk ROM (CD-ROM), digital versatile disks (DVDs) or other optical or magnetic storage devices, or any other medium that can be used to store the desired information and that can be accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

Figure 2:
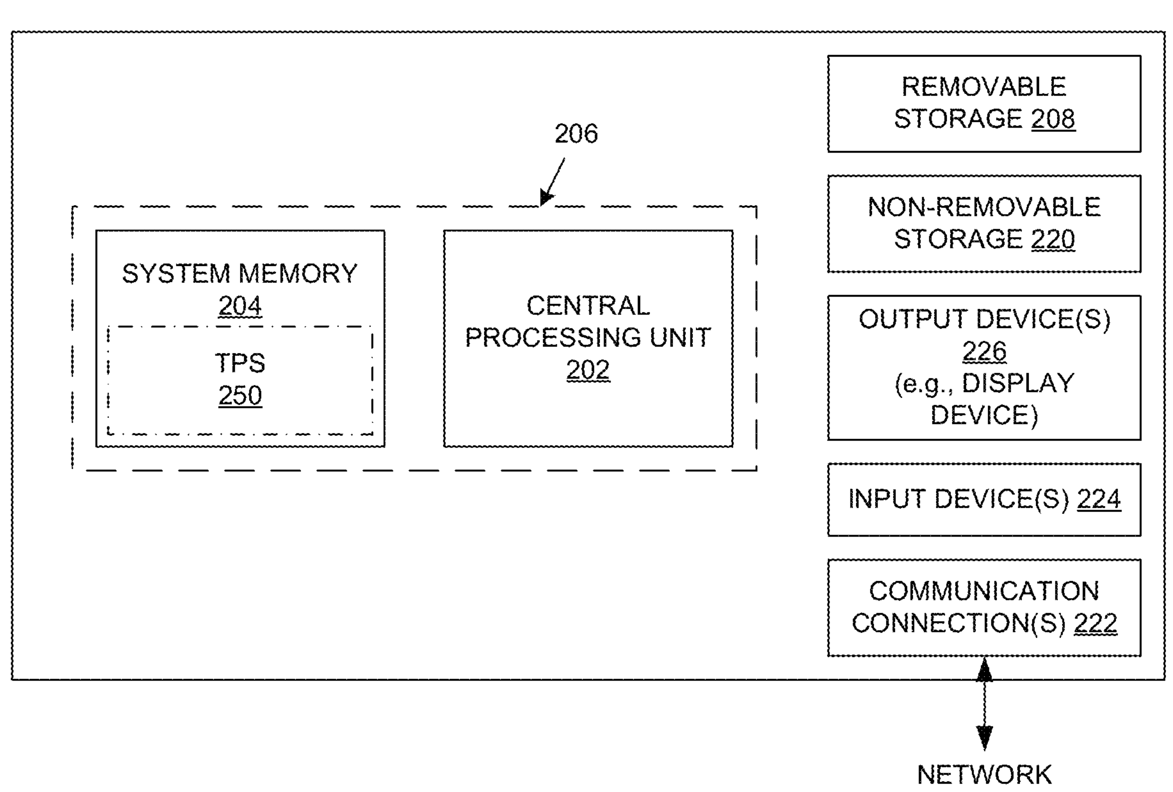
FIG. 2 is a block diagram of an example of a computer system upon which the embodiments described herein may be implemented.

FIG. 2 shows a block diagram of an example of a computer system 200 upon which the embodiments described herein may be implemented. In its most basic configuration, the system 200 includes at least one processing unit 202 and memory 204. This most basic configuration is illustrated in FIG. 2 by dashed line 206. The system 200 may also have additional features and/or functionality. For example, the system 200 may also include additional storage (removable and/or non-removable) including, but not limited to, magnetic or optical disks or tape. Such additional storage is illustrated in FIG. 2 by removable storage 208 and non-removable storage 220. The system 200 may also contain communications connection(s) 222 that allow the device to communicate with other devices, e.g., in a networked environment using logical connections to one or more remote computers.

The system 200 also includes input device(s) 224 such as a keyboard, mouse, pen, voice input device, touch input device, etc. Output device(s) 226 such as a display device, speakers, printer, etc., are also included. A display device may be, for example, a cathode ray tube display, a light-emitting diode display, or a liquid crystal display.

In the example of FIG. 2, the memory 204 includes computer-readable instructions, data structures, program modules, and the like associated with a treatment planning system (TPS) 250, which may also be referred to as an optimizer. However, the treatment planning system 250 may instead reside in any one of the computer storage media used by the computer system 200, or may be distributed over some combination of the computer storage media, or may be distributed over some combination of networked computers. The treatment planning system 250 is used to evaluate and produce a final (prescribed) treatment plan.

More specifically, a proposed radiation treatment plan is defined (e.g., using the treatment planning system 250 of FIG. 2), stored in a computer system memory, and accessed from that memory. The proposed radiation treatment plan includes values of parameters that can affect dose and dose rate, as well as other parameters. The parameters may also include angles (directions) of beams to be directed toward a treatment target, and a beam energy for each of the beams. The parameters may also include a schedule for applying the irradiations.

During treatment, in an example embodiment, a particle beam enters a nozzle of a radiotherapy machine, which includes one or more components that affect (e.g., decrease, modulate) the energy of the beam, to control the dose delivered by the beam and/or to control the dose versus depth curve of the beam, depending on the type of beam. For example, for a proton beam or an ion beam that has a Bragg peak, the nozzle can control the location of the Bragg peak in the treatment target laterally to the beam axis. In other embodiments, energy modulation is performed outside of the nozzle (e.g., upstream of the nozzle).

In embodiments according to the invention, the nozzle emits particles in a spot scanning beam (also referred to as a pencil beam). The nozzle is mounted on a moveable gantry so that the beam can be delivered from different directions (angles) relative to a patient (treatment target) on the patient support device, and the position of the patient support device relative to the beam may also be changed. The target area is irradiated with a raster scan by the spot scanning beam.

The beam can deliver a relatively high dose rate (a relatively high dose in a relatively short period of time). For example, if necessary, the beam can deliver at least 40 grays (Gy) in less than one second, and may deliver as much as 120 Gy per second or more.

Figure 3:
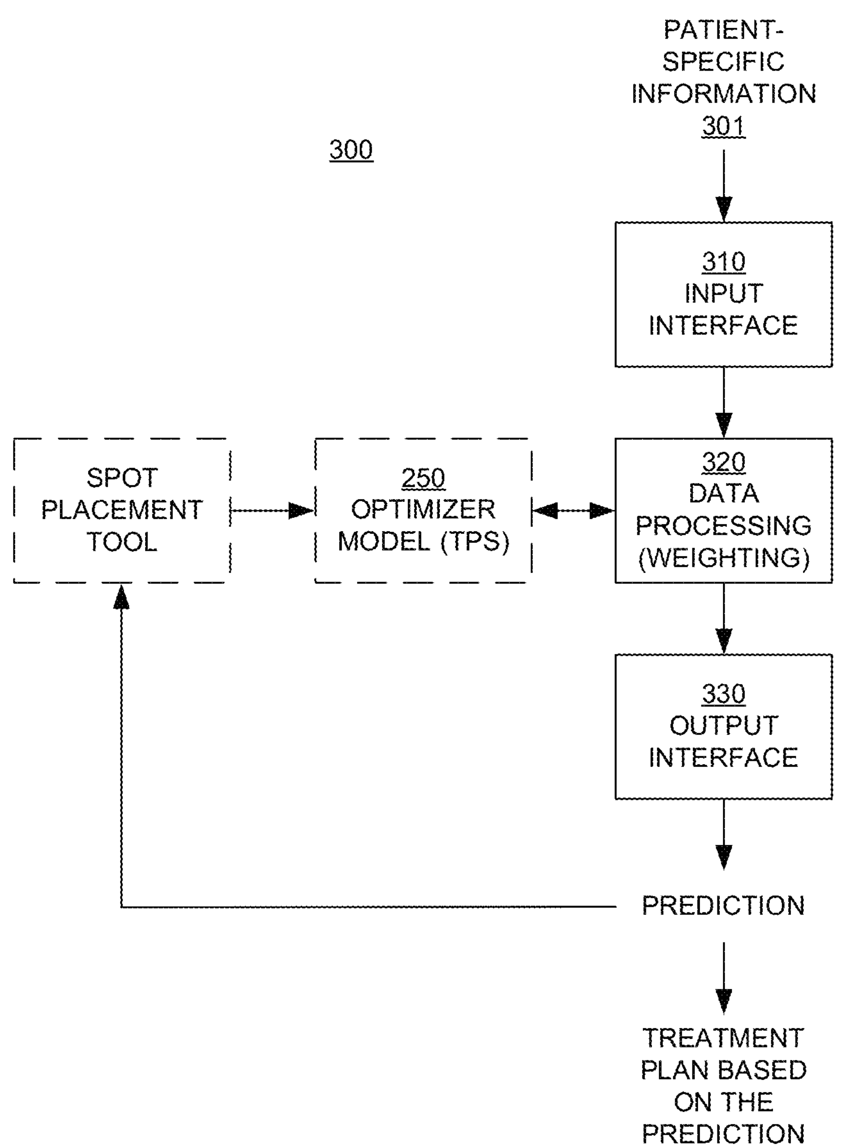
FIG. 3 is a block diagram illustrating an example of an automated radiation therapy treatment planning system with which the embodiments described herein may be implemented.

FIG. 3 is a block diagram illustrating an example of an automated radiation therapy treatment planning system 300 in embodiments according to the present invention. The system 300 includes an input interface 310 to receive patient-specific information (data) 301, a data processing component 320 that implements the treatment planning system 250, and an output interface 330. The system 300 in whole or in part may be implemented as a software program, hardware logic, or a combination thereof on/using the computer system 200 (FIG. 2).

In the example of FIG. 3, the patient-specific information 301 is provided to and processed by the treatment planning system 250, which yields a prediction result. A proposed radiation treatment plan based on the prediction result can then be generated.

The inputs to the data processing component 320 (e.g., the treatment planning system 250) include an initial pattern (or grid or placement) of spots in the treatment target. The initial spot pattern may itself be generated by a spot placement tool that is coupled to or is a component of the treatment planning system 250. As will be described further below, in embodiments according to the disclosed invention, the initial spot pattern for optimization in the treatment planning system 250 considers or is based on the size and/or shape of the treatment target. The treatment planning system 250 can then adjust the weights of the spots with respect to, for example, beam energy or dose rate. The goal is to determine a set of weights so that, during treatment, the treatment target will receive a homogenous dose (a uniform dose across the treatment target) and the delivered dose will conform more closely to the edges of the treatment target.

More specifically, the proposed radiation treatment plan is evaluated to determine whether or not objectives (e.g., clinical goals) that are specified for treatment of a patient are satisfied by the proposed radiation treatment plan. The clinical goals or objectives may be expressed in terms of a set of quality metrics, such as target homogeneity, conformity to the treatment target, critical organ sparing, and the like, with respective target values for the metrics.

If the treatment planning system 250 is unable to converge on a set of spot weights that satisfy those goals, then the initial spot pattern can be changed and the process just described can be repeated. Several satisfactory treatment plans may be determined, in which case the treatment plan that is judged as best satisfying the specified objectives (clinical goals) can be selected as the prescribed (final) treatment plan.

In radiation therapy techniques in which the intensity of the particle beam is either constant or modulated across the field of delivery, such as in intensity modulated particle therapy (IMPT), beam intensity is varied across each treatment region (each target volume in a treatment target) in a patient. The degrees of freedom available for dose modulation include, but are not limited to, beam shaping (collimation), beam weighting (spot scanning), number of energy layers, and angles of incidence (which may be referred to as beam geometry). For IMPT, steep dose gradients are often used at the target border and field edges to enhance dose conformity. This increases the complexity of fluence maps and decreases robustness of the treatment plan to uncertainties and changes in conditions (e.g., patient position and anatomy) over the course of the treatment period. These degrees of freedom lead to an effectively infinite number of potential treatment plans, and therefore consistently and efficiently generating and evaluating high-quality treatment plans is beyond the capability of a human and relies on the use of a computer system, particularly considering the time constraints associated with the use of radiation therapy to treat ailments like cancer, as well as the large number of patients that are undergoing or need to undergo radiation therapy during any given time period.

Embodiments according to the invention improve radiation treatment planning and the treatment itself. Treatment plans generated as described herein are superior for sparing healthy tissue from radiation in comparison to conventional techniques by optimizing the balance between the dose delivered to unhealthy tissue (e.g., a tumor) in a target volume in a treatment target and the dose delivered to surrounding healthy tissue. Treatment plans generated as described herein are also superior for providing a uniform dose across the entire treatment target in comparison to conventional techniques. Moreover, treatment plans generated as described herein are superior in terms of robustness in comparison to conventional techniques. Treatment planning, while still a complex task, is improved relative to conventional treatment planning.

Embodiments according to the invention are not necessarily limited to radiation therapy techniques such as IMPT.

Radiation Treatment Planning that Considers the Dimensions of a Treatment Target In overview, in embodiments according to the invention, the size and/or shape of the treatment target is considered when determining the placement and density of spots in a treatment target in the process of generating a radiation treatment plan. In embodiments, during treatment planning, the treatment target is separated into regions corresponding to different target volumes in the treatment target, and the placement and density of spots (the amount of spacing between spots) in each region is determined independently for each region according to the size and/or shape of the region.

Figure 4:
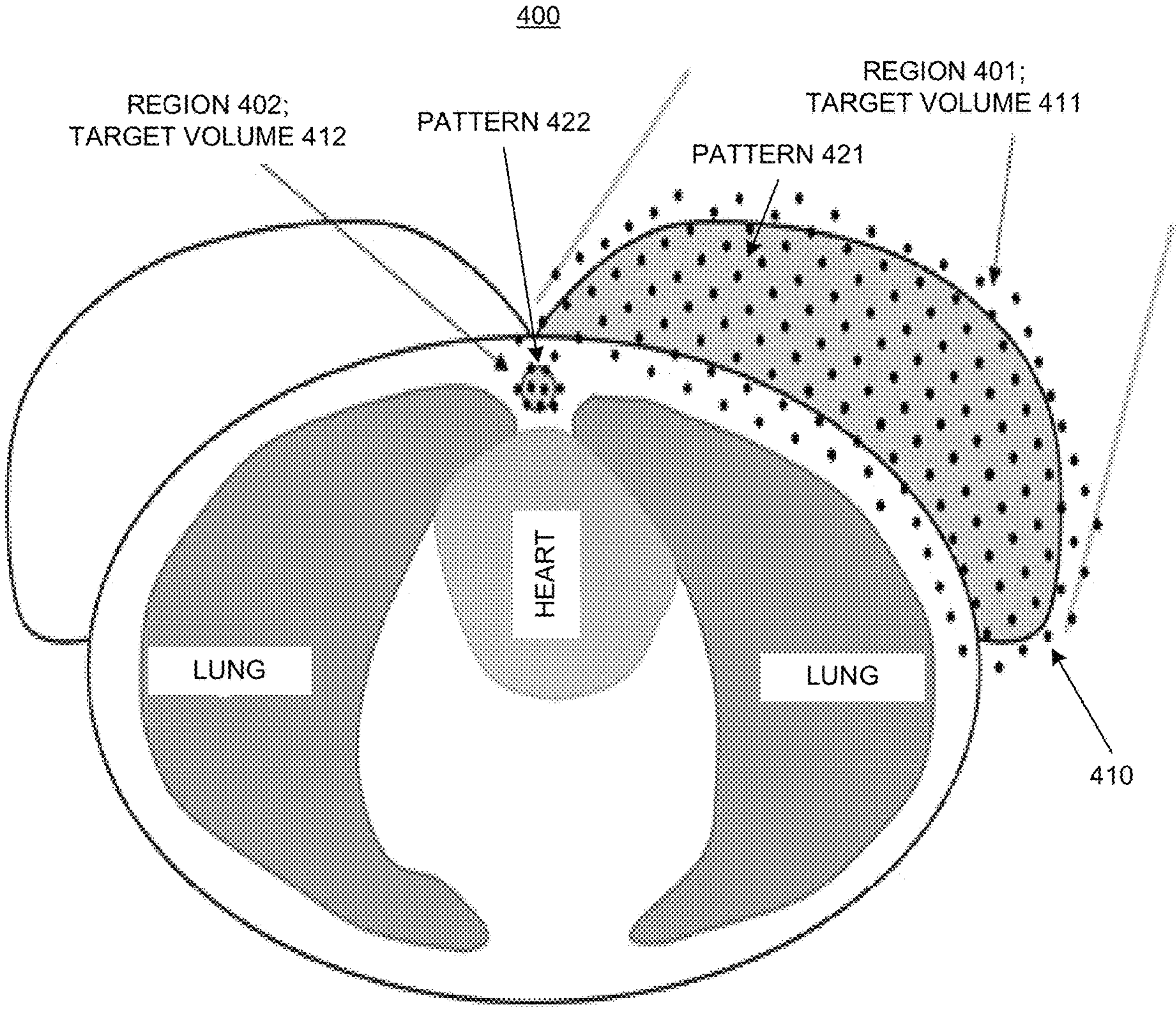
FIG. 4 illustrates an example of a cross-section of a treatment target that is modeled according to embodiments in accordance with the present invention.

FIG. 4 illustrates an example of a representation of a cross-section of a treatment target 400 in a patient that is modeled according to embodiments in accordance with the present invention. In the example of FIG. 4, the treatment target 400 is logically or virtually separated into regions 401 and 402 corresponding to, respectively, the physical target volumes 411 (e.g., a breast) and 412 (e.g., a node near the breast) in the treatment target. In other words, for the purpose of treatment planning, the treatment target 400 is represented as regions 401 and 402. In this example, the regions 401 and 402 are separated from each other; that is, there is tissue (e.g., healthy tissue) between the two regions. Also, the region 402 is smaller than the region 401.

In embodiments, the treatment target is separated into regions or segments using an automatic segmentation tool. Alternatively, the treatment target can be separated into regions or segments by a clinician.

In FIG. 4, each dot (e.g., the dot 410) represents a spot or location in the treatment target for spot scanning with a radiation beam. In embodiments according to the invention, the placement and density of spots (the amount of spacing between spots) in each of the regions 401 and 402 are determined independently for each region according to the size and/or shape of the region. For example, the amount of distance between spots in the region 401 corresponding to the larger target volume 411 can be greater than the amount of distance between spots in the region 402 corresponding to the smaller target volume 412. That is, the smaller region/target volume 402/412 has a higher density of spots relative to the larger region/target volume 401/411. In other words, the smaller region/target volume 402/412 has a finer spot grid or pattern 422 relative to that of the larger region/target volume 401/411, and conversely the larger region/target volume has a coarser spot grid or pattern 421 relative to that of the smaller region/target volume.

The spot patterns 421 and 422 can be used as initial conditions that are input into the treatment planning system 250 to generate a radiation treatment plan as described above in conjunction with FIG. 3. Accordingly, the treatment planning system 250 can independently optimize the weights of the spots in each region/target volume of the treatment target 400 to achieve a uniform dose in each target volume during treatment. Spots that are, for example, far outside of a region/target volume can be assigned a weight of zero, so that the delivered dose will conform closely to the boundaries of the treatment target.

While the example of FIG. 4 includes two regions, the present invention is not so limited.

Figure 5:
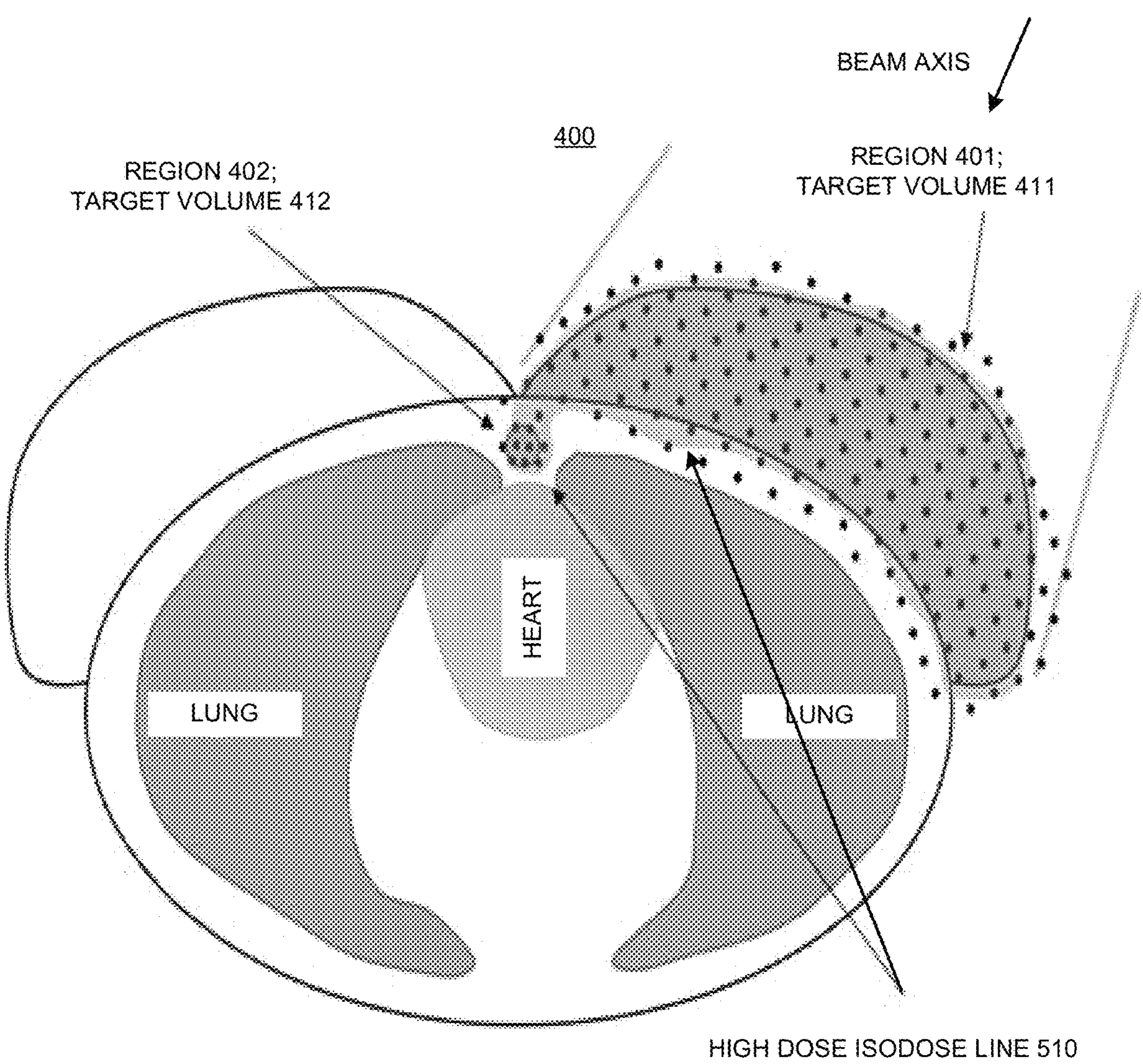
FIG. 5 illustrates an example of a high-dose isodose line of a treatment target that is modeled according to embodiments in accordance with the present invention.

FIG. 5 illustrates an example of a high-dose isodose line 510 of the treatment target 400 determined according to embodiments in accordance with the present invention. The high-dose isodose line 510 corresponds to the boundaries of the lighter-gray area that is outside of the darker-gray region/target volume 401/411 and the region/target volume 402/412. As shown, in addition to receiving a homogenous dose, the delivered dose conforms closely to the edges of the target volumes 421 and 422 and hence to the edges of the entire treatment target 400. Accordingly, nearby organs-at-risk (e.g., the heart and lungs) are spared from receiving a dose of radiation.

Figure 6:
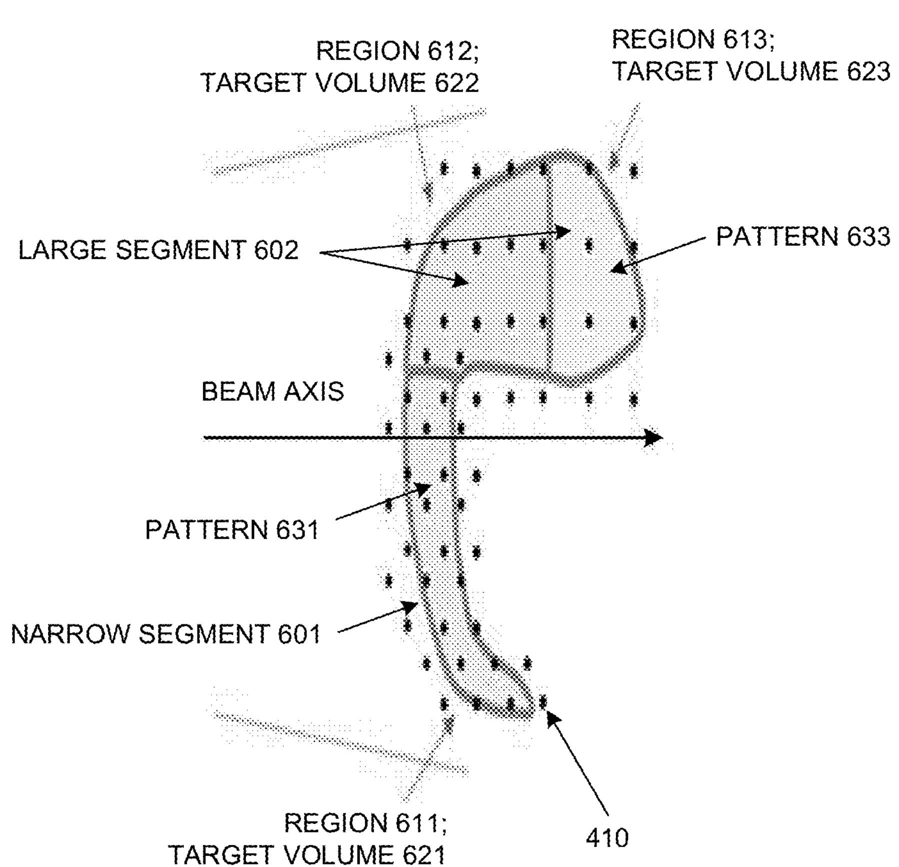
FIG. 6 illustrates an example of a cross-section of a treatment target that is modeled according to embodiments in accordance with the present invention.

FIG. 6 illustrates an example of a cross-section of a treatment target 600 that is modeled according to embodiments in accordance with the present invention. Generally speaking, the treatment target 600 has a more complex shape than that of the treatment target 400 of FIG. 4. In the example of FIG. 6, the treatment target 600 includes a relatively narrow segment 601 extending from a relatively larger (e.g., wider) segment 602. In this example, the target volume 600 is logically or virtually separated into regions 611, 612, and 613 corresponding to the segments 601 and 602 in the treatment target 600. In other words, for the purpose of treatment planning, the treatment target 600 is represented as regions 611, 612, and 613. In this example, the regions 611, 612, and 613 are not physically separated from each other. Also, in this example, the region 612 can be thought of as the region where the regions 611 and 613 would overlap each other if the latter regions were to be extended.

The regions 611, 612, and 613 correspond to physical target volumes 621, 622, and 623, respectively, in the treatment target 600. Similar to the example of FIG. 4, the placement and density of spots (the amount of spacing between spots) in each of the regions 611, 612, and 613 of FIG. 6 are determined independently for each region according to the size and/or shape of the region. For example, the amount of distance between spots in the region 613 corresponding to the larger (e.g., wider) target volume 623 can be greater than the amount of distance between spots in the region 611 corresponding to the smaller target volume 621. That is, the smaller region/target volume 611/621 has a higher density of spots relative to the larger region/target volume 613/623. In other words, the smaller region/target volume 611/621 has a finer spot grid or pattern 631 relative to that of the larger region/target volume 612/623, and conversely the larger region/target volume has a coarser spot grid or pattern 633 relative to that of the smaller region/target volume.

With regard to the region 612, in some embodiments, the placement and spacing of the spots is the same as either the region 611 or the region 613. For example, it may be advantageous to use a finer (denser) spot pattern in the region 612; however, because there are more spots, the dose delivery time will be longer. On the other hand, it may be advantageous to use as few as spots as possible in the treatment target 600 to reduce the dose delivery time, in which case a coarser spot pattern may be used in the region 612; however, while this may reduce the dose delivery time, it may also introduce a need for additional intermediate energy layers, which may offset some or all of the reduction in dose delivery time or even increase dose delivery time.

In general, the number and density of spots in an intermediary (in-between or transitional) region like the region 612 can be determined on a case-by-case basis depending on which of these competing objectives (number of spots versus density of spots) results in a better treatment plan. The amount of spacing in the region 612 can be different from both the amount of spacing in the first pattern and the amount of spacing in the second pattern, or it can be the same as that of one of the first pattern or the second pattern.

While the example of FIG. 6 includes three regions, the present invention is not so limited.

The above examples describe spot placement according to the size and/or shape of the target volumes in a treatment target. Embodiments according to the present invention can also be applied to the spacing of energy layers, which may be integrated with the placement of spots.

Figure 7:
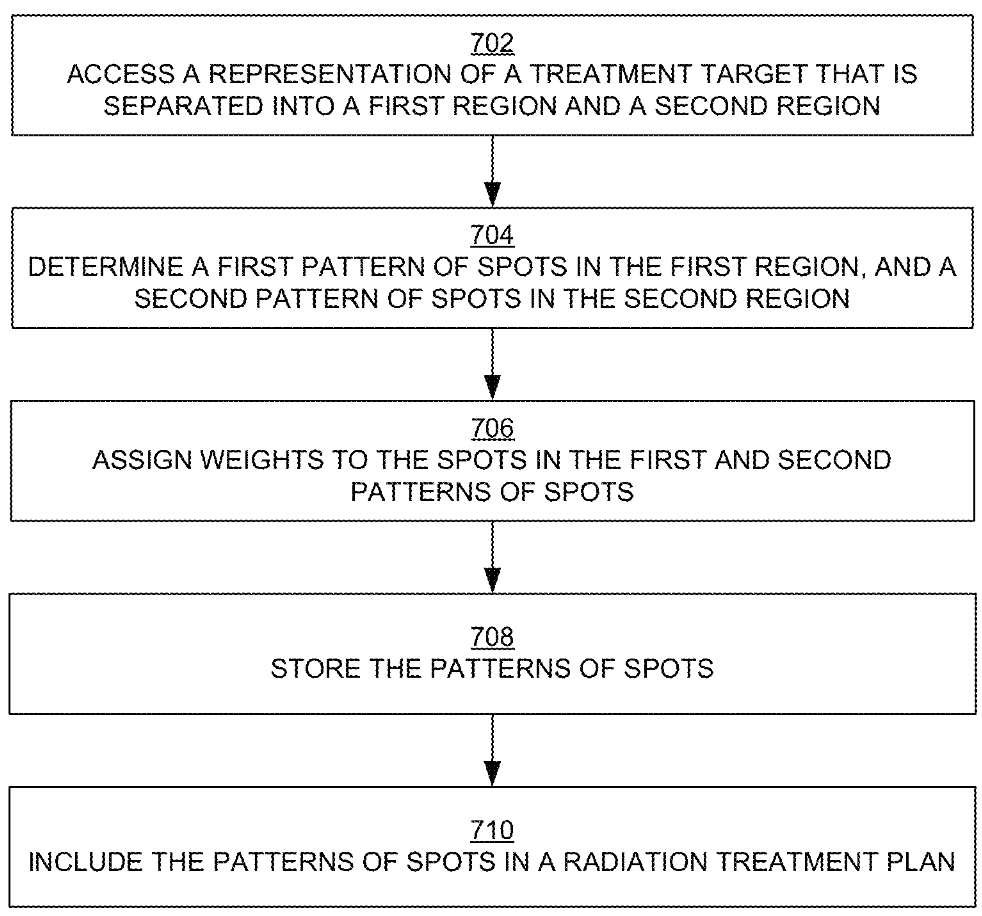
FIG. 7 is a flowchart of an example of a computer-implemented method for radiation treatment planning in embodiments according to the present invention.

FIG. 7 is a flowchart 700 of an example of a computer-implemented method for radiation treatment planning in embodiments according to the present invention. The flowchart 700 can be implemented as computer-executable instructions (e.g., the treatment planning system 250 of FIGS. 2 and 3) residing on some form of computer-readable storage medium (e.g., in memory of the computer system 200 of FIG. 2).

While the operations in the flowchart of FIG. 7 are presented as occurring in series and in a certain order, the present invention is not so limited. The operations may be performed in a different order and/or in parallel, and they may also be performed in an iterative manner. As noted above, because of the different parameters that need to be considered, the range of values for those parameters, the interrelationship of those parameters, the need for treatment plans to be effective yet minimize risk to the patient, and the need to generate high-quality treatment plans quickly, the use of the treatment planning system 250 executing consistently on the computer system 200 (FIG. 2) for radiation treatment planning as disclosed herein is important.

FIG. 7 is discussed with reference to the examples of FIGS. 4 and 6.

In block 702 of FIG. 7, a representation of a treatment target (e.g., the treatment target 400 or 600) is accessed. The treatment target is logically or virtually separated into at least a first region and a second region (e.g., the regions 401 and 402, or the regions 611, 612, and 613), where the first region and the second region have different physical dimensions (e.g., different sizes and/or shapes). The first region and the second region correspond to respective physical target volumes in the treatment target. The first region and the second region may or may not be physically separated from each other.

In block 704, a first pattern of spots (e.g., the pattern 421 or the pattern 633) inside the first region is determined. Also, a second pattern of spots (e.g., the pattern 422 or the pattern 631) inside the second region is determined. The amount of spacing between the spots (the density of the spots; first density) in the first pattern is based on or corresponds to the dimensions of the first region, and the amount of spacing between the spots (second density) in the second pattern is based on or corresponds to the dimensions of the second region.

For example, when the first region is smaller than the second region, then the amount of spacing between the spots in the first pattern is less than the amount of spacing between the spots in the second pattern. For example, when the first region is narrower than the second region in at least one of the dimensions (e.g., it is narrower in at least one of the x-, y-, and z-directions), then the amount of spacing between the spots in the first pattern is less than the amount of spacing between the spots in the second pattern.

In embodiments, the first pattern of spots and the second pattern of spots are initial conditions that are input into a treatment planning system (e.g., the treatment planning system 250 of FIGS. 2 and 3). In such embodiments, a respective value of a weight is assigned to each spot in the first pattern of spots and to each spot in the second pattern of spots. Then, in block 706, a determination is made as to whether an objective (e.g., dose distribution) defined for the radiation treatment is satisfied using the values of the weights assigned to the first pattern of spots and the second pattern of spots. One or more of the values of the weights can be adjusted (e.g., iteratively) when the objective is not satisfied; if the objective is satisfied, then the values of the weights are stored in memory of a computer system (e.g., the computer system 200 of FIG. 2). If the objective cannot be satisfied even after the values of the weights are adjusted, then either or both of the first pattern of spots and the second pattern of spots can be adjusted. That is, a new first pattern and/or a new second pattern can be determined, including a change in the number of spots or in the density of the spots (block 704), and the operations of block 706 are repeated for the new first and/or second pattern(s) of spots.

In block 708, the first pattern of spots and the second pattern of spots that are output from block 706 are stored in memory of a computer system (e.g., the computer system 200 of FIG. 2).

In block 710, the first pattern of spots and the second pattern of spots that have been stored in memory can be included in a radiation treatment plan.

In some instances, the representation of the treatment target also separates the treatment target into a third region that is adjacent to both the first and second regions (see the example of FIG. 6). In those instances, in embodiments, the amount of spacing between the spots in a third pattern of spots inside the third region is the same as either the amount of spacing in the first pattern or the amount of spacing in the second pattern. In other embodiments, the amount of spacing in the third region is different from both the amount of spacing in the first pattern and the amount of spacing in the second pattern. In instances in which there is a third region (or more than two regions), the method of FIG. 7 can be readily extended to those additional regions; the method of FIG. 7 is not limited to two regions.

In summary, the disclosed methodologies can provide spot locations that are conformal with the outlines of the treatment target and the target volumes inside the treatment target, yielding sharper lateral penumbras and better dose distributions within the treatment target. Consequently, during radiation treatment, surrounding healthy tissue is spared from radiation, and dose variations within the treatment target in general and the target volumes in particular are avoided. The methodologies disclosed herein can be particularly useful for FLASH radiation therapy in which a relatively high therapeutic radiation dose is delivered to the target within a single, short period of time. In general, use of the modeling methodologies that are aware of and account for the sizes and/or shapes of target volumes in a treatment target as disclosed herein can improve upon previous spot placement schemes.

Treatment plans generated as described herein are superior for sparing normal tissue from radiation in comparison to conventional techniques by reducing, if not minimizing, the magnitude (and the integral in some cases) of the dose to normal tissue (e.g., tissue that is outside the treatment target) by design. Treatment planning, while still a complex task of finding a balance between competing and related parameters, is simplified relative to conventional planning. The methodologies disclosed herein may also be useful for stereotactic radiosurgery as well as stereotactic body radiotherapy with single or multiple metastases.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer system, comprising:

a memory storing instructions; and a processor configured to execute the instructions to cause the computer system to perform a method for planning radiation treatment, the radiation treatment including spot scanning of a treatment target, and the method including accessing a representation of the treatment target in which the treatment target is separated into at least a first region and a second region, first physical dimensions of the first region being different from second physical dimensions of the second region, determining a first pattern of first spots inside the first region, an amount of spacing between the first spots in the first pattern being based on the first physical dimensions, determining a second pattern of second spots inside the second region, an amount of spacing between the second spots in the second pattern being based on the second physical dimensions; and storing, in the memory, the first pattern and the second pattern for access by a radiotherapy machine configured to perform the spot scanning of the treatment target based on a radiation treatment plan, the radiation treatment plan being based on the first pattern and the second pattern.

2. The computer system of claim 1, wherein the first region is smaller than the second region; and the amount of spacing between the first spots in the first pattern is less than the amount of spacing between the second spots in the second pattern.

3. The computer system of claim 1, wherein the first region is narrower than the second region in at least one dimension; and the amount of spacing between the first spots in the first pattern is less than the amount of spacing between the second spots in the second pattern.

4. The computer system of claim 1, wherein the first pattern and the second pattern correspond to initial conditions; and the method further comprises assigning values of weights to each of the first spots and each of the second spots, determining whether an objective defined for the radiation treatment is satisfied using the values of the weights, and adjusting one or more of the values of the weights in response to determining the objective is not satisfied.

5. The computer system of claim 1, wherein the first pattern and the second pattern correspond to initial conditions; and the method further comprises assigning values of weights to each of the first spots and each of the second spots, determining whether an objective defined for the radiation treatment is satisfied using the values of the weights, and adjusting at least one of the first pattern or the second pattern in response to determining the objective is not satisfied.

6. The computer system of claim 1, wherein the first region and the second region are physically separated from each other.

7. The computer system of claim 1, wherein the representation of the treatment target separates the treatment target into the first region, the second region and a third region, the third region being adjacent to both the first region and the second region; and an amount of spacing between third spots in a third pattern inside the third region is the same as one of the amount of spacing between the first spots in the first pattern, or the amount of spacing between the second spots in the second pattern.

8. The computer system of claim 1, wherein the determining the first pattern is based on a size or a shape of the first region; and the determining the second pattern is based on a size or a shape of the second region.

9. A non-transitory computer-readable storage medium storing computer-executable instructions that, when executed by a processor of a computer system, cause the computer system to perform a method for planning radiation treatment, the radiation treatment including spot scanning of a treatment target, and the method including accessing a representation of the treatment target in which the treatment target is separated into at least a first region and a second region, a first area of the first region being different from a second area of the second region, determining a first pattern of first spots inside the first region, a density of the first spots in the first pattern being based on the first area, determining a second pattern of second spots inside the second region, a density of the second spots in the second pattern being based on the second area, and storing, in a memory, the first pattern and the second pattern for access by a radiotherapy machine configured to perform the spot scanning of the treatment target based on a radiation treatment plan, the radiation treatment plan being based on the first pattern and the second pattern.

10. The non-transitory computer-readable storage medium of claim 9, wherein the first region is smaller than the second region; and the density of the first spots in the first pattern is greater than the density of the second spots in the second pattern.

11. The non-transitory computer-readable storage medium of claim 9, wherein a first dimension of the first region is less than a second dimension of the second region, the first dimension corresponding to the second dimension; and the density of the first spots in the first pattern is greater than the density of the second spots in the second pattern.

12. The non-transitory computer-readable storage medium of claim 9, wherein the first pattern and the second pattern correspond to initial conditions; and the method further comprises assigning values of weights to each of the first spots and each of the second spots, determining whether an objective defined for the radiation treatment is satisfied using the values of the weights, and adjusting one or more of the values of the weights in response to determining the objective is not satisfied.

13. The non-transitory computer-readable storage medium of claim 9, wherein the first pattern and the second pattern correspond to initial conditions; and the method further comprises assigning values of weights to each of the first spots and each of the second spots, determining whether an objective defined for the radiation treatment is satisfied using the values of the weights, and adjusting at least one of the first pattern or the second pattern in response to determining the objective is not satisfied.

14. The non-transitory computer-readable storage medium of claim 9, wherein the representation of the treatment target separates the treatment target into the first region, the second region and a third region, the third region being adjacent to both the first region and the second region; and a density of third spots in a third pattern inside the third region is the same as one of the density of the first spots in the first pattern, or the density of the second spots in the second pattern.

15. A computer-implemented method for planning radiation treatment, the radiation treatment including spot scanning of a treatment target, and the computer-implemented method comprising:

accessing a description of the treatment target according to which the treatment target is virtually separated into at least a first region and a second region, first physical dimensions of the first region being different from second physical dimensions of the second region;

determining a first density of first spots inside the first region based on the first physical dimensions;

determining a second density of second spots inside the second region based on the second physical dimensions, the second density being different from the first density;

determining a first pattern for the first spots in the first region, the first spots in the first pattern having at least the first density;

determining a second pattern for the second spots in the second region, the second spots in the second pattern having at least the second density; and storing, in a memory, the first pattern and the second pattern for access by a radiotherapy machine configured to perform the spot scanning of the treatment target based on a radiation treatment plan, the radiation treatment plan being based on the first pattern and the second pattern.

16. The computer-implemented method of claim 15, wherein the first region is smaller than the second region; and the first density is greater than the second density.

17. The computer-implemented method of claim 15, wherein the first region is narrower than the second region in at least one dimension; and the first density is greater than the second density.

18. The computer-implemented method of claim 15, wherein the first pattern and the second pattern correspond to initial conditions; and the computer-implemented method further comprises assigning values of weights to each of the first spots and each of the second spots, determining whether an objective defined for the radiation treatment is satisfied using the values of the weights, and adjusting one or more of the values of the weights in response to determining the objective is not satisfied.

19. The computer-implemented method of claim 15, wherein the first pattern and the second pattern correspond to initial conditions; and the computer-implemented method further comprises assigning values of weights to each of the first spots and to each of the second spots, determining whether an objective defined for the radiation treatment is satisfied using the values of the weights, and adjusting at least one of the first density or the second density in response to determining the objective is not satisfied.

20. The computer-implemented method of claim 15, wherein the first region and the second region are physically separated from each other; and the determining the first density and the determining the second density are performed concurrently with and independently of each other.

21. The computer-implemented method of claim 15, wherein the treatment target is virtually separated into the first region, the second region and a third region that is adjacent to both the first region and the second region; and a density of third spots in a third pattern inside the third region is the same as one of the first density or the second density.

* * * * *